United States Patent [19]

Harker et al.

[11] Patent Number: 4,929,602

[45] Date of Patent: May 29, 1990

[54] METHOD OF INHIBITING PLATELET DEPENDENT ARTERIAL THROMBOSIS

[75] Inventors: Laurence A. Harker, San Diego; Stephen R. Hanson, Encinitas, both of Calif.

[73] Assignee: Scripps Clinic and Research Foundation, La Jolla, Calif.

[21] Appl. No.: 275,330

[22] Filed: Nov. 22, 1988

Related U.S. Application Data

[63] Continuation-in-part of Ser. No. 125,178, Nov. 25, 1987, abandoned.

[51] Int. Cl.$^5$ .................... A61K 37/02; C07K 5/08
[52] U.S. Cl. ........................................ 514/18; 530/331
[58] Field of Search ..................... 514/18; 530/331

[56] References Cited

U.S. PATENT DOCUMENTS 4,318,904 3/1982 Shaw et al. .................... 530/331

*Primary Examiner*—Lester L. Lee
*Attorney, Agent, or Firm*—Dressler, Goldsmith, Shore, Sutker & Milnamow, Ltd.

[57] ABSTRACT

The present invention contemplates a method of preventing platelet dependent arterial thrombosis using a halogen-methyl ketone-containing peptide represented by Formula (1) as shown in FIG. 1, or a hydrohalic addition product thereof. More particularly, the present invention provides improved methods for inhibiting arterial restenosis, hemodialysis and the like.

21 Claims, 7 Drawing Sheets

FIG. 3A
FIG. 3B
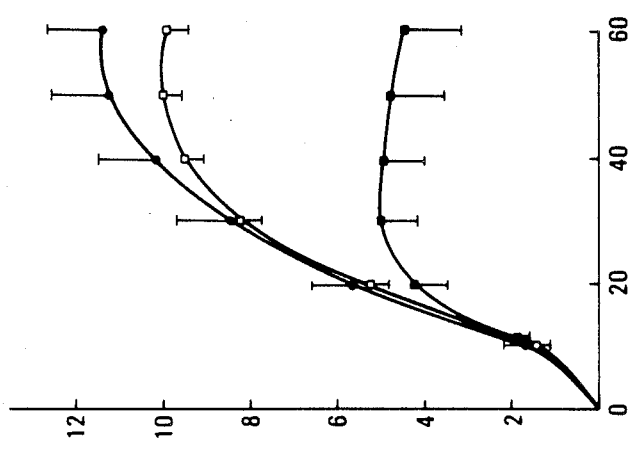
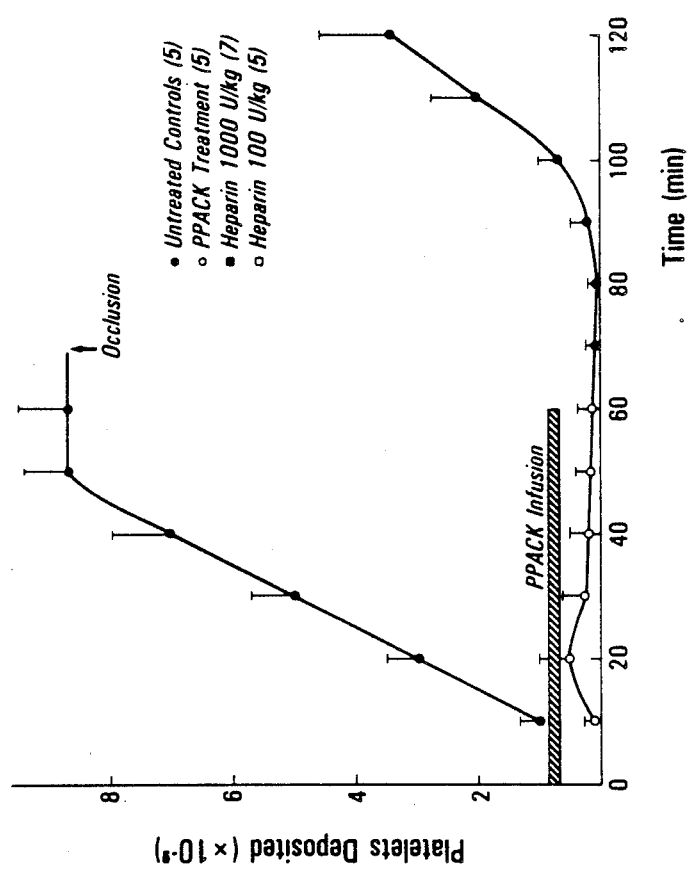

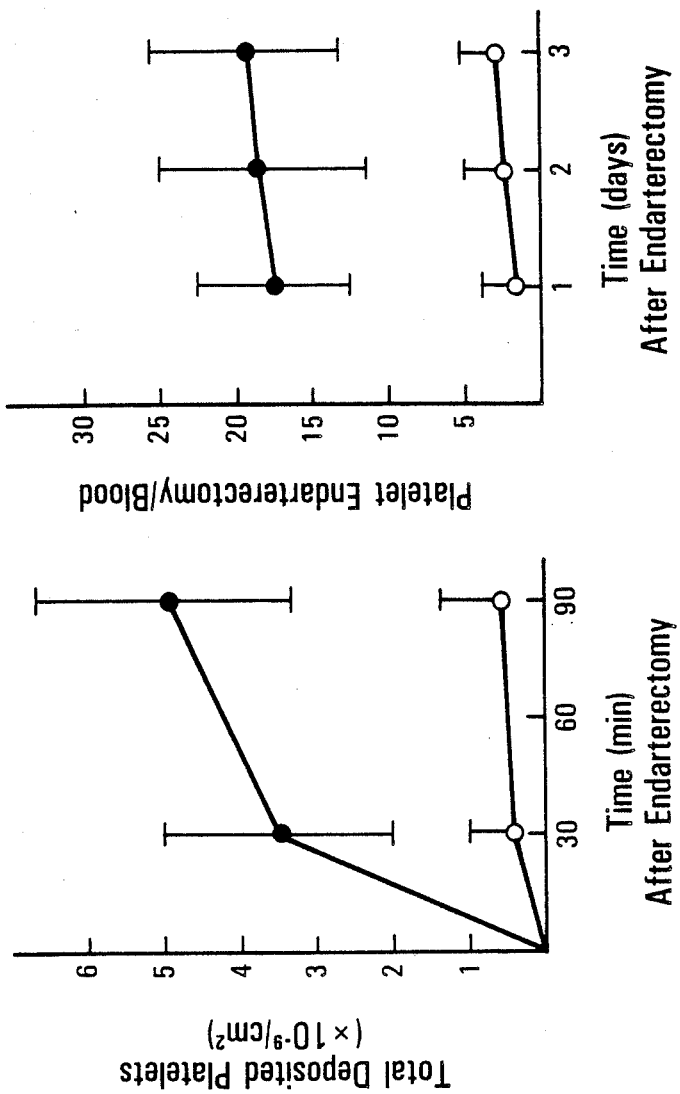

METHOD OF INHIBITING PLATELET DEPENDENT ARTERIAL THROMBOSIS

This invention was made with the support of the United States Government, and the United States Government has certain rights in the invention.

CROSS REFERENCE TO RELATED APPLICATION

This is a continuation-in-part of application Ser. No. 125,178, filed Nov. 27, 1987 and now abandoned, the disclosure of which is hereby incorporated by reference.

DESCRIPTION

1. Technical Field

The present invention relates to the use of a halogenmethyl ketone containing peptide to inhibit platelet aggregation in patients at risk for arterial thrombosis.

2. Background

A thrombus is an aggregate of elements formed in the living heart or vessels from constituents of the blood in response to a thrombogenic stimulus.

Thrombosis, the process of thrombus formation, can occur through distinct but usually interactive mechanisms. The first, platelet aggregation, occurs as a result of platelets being activated by a thrombogenic stimulus such as a vessel wall lesion. The second, fibrin formation, is the result of activation of the coagulation cascade system whose final step is typically considered the conversion of fibrinogen into fibrin by thrombin, i.e., fibrin formation. The purpose of fibrin formation appears to be to stabilize the aggregated platelets so as to stabilize the hemostatic plug.

The magnitude or degree of participation of platelet aggregation and fibrin formation is now known to vary as a result of hemodynamic (blood flow) factors. For instance, venous thrombosis occurs under low flow rate conditions and has been shown to involve a combined and equivalent consumption of platelets and elements of the coagulation cascade system. Harker et al., *N. Eng. J. Med.*, 287:999–1005 (1972). As a result, venous thrombi are typically unstructured masses composed of a relatively few aggregated platelets, a large amount of interspersed fibrin and some red blood cells, hence the name "red thrombus". See Freiman, In "Hemostasis and Thrombosis: Basic Principles and Clinical Practice", Coleman et al. (eds.) 2nd Ed., Philadelphia, J. B. Lippincott Co., pp. 1123-35 (1987). These observations suggest that fibrin formation plays the predominant role in venous thrombus development.

In contrast, arterial thrombosis occurs under high flow rate conditions and has been shown to involve, at least in its early stages, selective consumption of platelets. Harker et al., *N. Eng. J. Med.*, 287:999–1005 (1972). For example, animal studies have shown that the prosthetic surface of plastic arteriovenous cannulas produce thrombi that are composed entirely of platelets, the thrombogenic process proceeding without detectable participation of the coagulation cascade system. Evans et al., *J. Exp. Med.*, 128:877–894 (1968), and Harker et al., *J. Clin,. Invest.*, 64:559–569 (1979). Presumably, fibrin formation is only minimal in arterial thrombosis because procoagulant material, such a thrombin, is swept away from the thrombogenic focus by the rapid arterial flow before coagulation becomes fully activated. As a result, arterial thrombi are typically either composed entirely of platelets (a "white thrombus") or are a complex structure composed of a basal or primary mass of platelets and a secondary mass of platelets and fibrin that overlays, and extends downstream from, the primary mass. See Freiman, supra. In either case, platelet aggregation at the site of a lesion is the predominant mechanism of arterial thrombus development. Therefore, arterial thrombosis, at least in its early stages, can be characterized as being platelet dependent. Harker et al., In "Vascular Diseases: Current Research and Clinical Application", Strandess et al., (eds.) Orlando, Grune & Stratton, pp. 271-283 (1987).

In view of the foregoing, it is not surprising that the therapeutic effectiveness of agents that affect either platelet aggregation or fibrin formation has been found to depend on the type of thrombosis being treated.

For instance, agents such as aspirin or dipyridamole that inhibit platelet function, i.e., inhibit the ability of platelets to aggregate, are effective in preventing arterial thrombosis but are not effective in treating stasis-type venous thrombosis. Conversely, agents such as heparin and hirudin that inhibit the ability of thrombin to form fibrin have been shown to be therapeutically effective against stasis-type venous thrombosis but not arterial thrombosis. Harker et al., *Thromb. Diath. Haemorrh.*, 31:188-203 (1974).

Thus, the art teaches that the emphasis in effective management of arterial thrombosis should be on regulating platelet aggregation as opposed to fibrin formation. That is, therapeutically effective inhibition of platelet dependent arterial thrombosis requires administration of agents that inhibit the ability of platelets to aggregate (platelet function inhibitors) as opposed to agents that inhibit fibrin formation per se (anticoagulants). Ideally, a clinically useful platelet-modifying drug should be nontoxic, have sustained action and have good antithrombotic potency without excessive risk of abnormal bleeding. None of the currently available clinical agents satisfies all these requirements. Aspirin, sulfinpyrazone, dipyridamole, suloctidil and ticlopidine are agents that have been evaluated in clinical trials to date.

One of the difficulties in developing agents capable of inhibiting platelet dependent arterial thrombosis is that platelets can be induced to aggregate by a variety of stimuli, including adenosine diphosphate (ADP), collagen, thrombin, thromboxane $A_2$, epinephrine, serotonin, vasopressin, antigen-antibody complexes, plasmin, viruses, bacterial, endotoxin and cancer cells. According to the art, it is probable that in vivo, the local concentration of any individual stimulant is probably not high enough to cause aggregation. As a result, it is probable that in vivo, several stimuli act on platelets simultaneously with synergistic effects so that very low individual concentrations of the stimuli may be effective to induce aggregation. See Packham, *Thromb. Haemostas.*, 50:610–619 (1983).

Thus, the art suggests that contravention of a particular platelet aggregation-inducing stimulus may not be an effective approach to inhibiting platelet dependent arterial thrombosis. Several studies support this point of view, the most relevant being those that have examined thrombin's humoral activity, i.e., its ability to stimulate platelet activation, as opposed to its enzymatic activity. For example, heparin and hirudin, well known anticoagulants, has also been shown to inhibit the ability of thrombin to stimulate platelet aggregation in vitro., Markwardt et al., *Haemostasis.*, 13:227-233 (1983), and Hoffman et al., *Haemostasis.*, 14:164-169 (1984). However, neither heparin or hirudin is effective in preventing arterial thrombosis in vivo, suggesting that one or more stimuli other than thrombin are responsible for inducing arterial platelet aggregation in vivo.

Of particular interest to the present invention is the tripeptide derivative D-phenylalanyl-L-propyl-L-arginyl-chloromethyl ketone (D-Phe Pro-Arg-Ch$_2$Cl or PPACK). Kettner et al., *Thromb. Res.*, 14:969-973 (1979), and U.S. Pat. No. 4,318,904, Mar. 9, 1982, Shaw et al. PPACK irreversibly inhibits that the enzymatic activity of thrombin by alkylating a histidine residue near its active site with an overall rate constant ($1.1 \times 10^7$ L/mol/sec) that is similar to that between the heparin-antithrombin III complex and thrombin.

Like heparin and hirudin, PPACK has been shown to inhibit thrombin's ability to convert plasma fibrinogen in fibrin and thereby induct formation of a red thrombus in vivo. See Kettner et al., *Thromb. Res.*, 14:969-973 (1979). However, it should be noted that the extremely high local concentration of thrombin produced by injection as described in each of the cited studies probably does not occur during any natural thrombotic process. In addition, the methodology of those studies does not permit a delineation of the relative contributions of thrombin's enzymatic and humoral activities in producing thrombosis under the experimental conditions reported. Thus, those studies did not use a model relevant for drawing conclusion about the affects of PPACK on arterial thrombosis.

The ability of PPACK to prevent fibrin formation has been shown to rapidly degrade in human plasma and in the blood of laboratory animals. For instance, Collen et al., *J. Lab. Clin. Med.*, 99:76-83 (1982) reported that the half-life of PPACK's ability to inhibit fibrin formation is rabbits is about 2.9 minutes. See, also, Hauptman et al., *Thromb. Res.*, 20:347-351 (1980).

Because of the relatively short half-like of PPACK's ability to inhibit fibrin formation in rabbit plasma, Collen et al., supra. concluded that the maintenance of PPACK's anticoagulant effect over longer periods of time would require its continuous infusion. In addition PPACK's short plasma half-life led Collen et al. to suggest that PPACK might be particularly useful in some emergency conditions where disseminated intravascular coagulation was suspected. Their reasoning was that a bolus injection of PPACK would rapidly inhibit the enzymatic activity of thrombin but would not result in a prolonged anticoagulant effect because its capacity to inhibit fibrin formation would be rapidly degraded.

Markwardt, *Ann N.Y. Acad. Sci.*, 485:204-214 (1986) has reported that the relatively short half-life of PPACK is due to its ability to form stable covalent bonds not only with thrombin, but also with other constituents of blood and tissue containing amino or thiol groups. According to Markwardt, that property makes PPACK unsuited for in vivo use as an anticoagulant. See, also, Hauptman et al., *Thromb. Res.*, 20:347-351 (1980).

For descriptions of the use of PPACK as a heparin-like anticoagulant in vitro, see Mohler et al., *Thromb. Haemostas.*, 56:160-164 (1986) and Bode et al., *Vox Sang.*, 51:192-196 (1986). Tiefenbrunn et al., *Circulation*, 73:1291-1299 (1986); Ku, *J. Car. Pharm.*, 8:29-36 (1986); Ofosu et al., *Ann. N.Y. Acad. Sci.*, 485:41-55 (1986); and Schaeffer et al., *J. Lab. Clin. Med.*, 107:488-497 (1986).

Also like heparin and hirudin, PPACK has been shown to inhibit the ability of thrombin to stimulate platelet activation in vitro. See Harmon et al., *J. Bio. Chem.*, 261:15928-33 (1986), Harmon et al., *Ann. N.Y. Acad. Sci.*, 485:387-395 (1986) and Markwardt et al., *Haemostasis* 13:227-233 (1983). However, each of those studies was performed using citrate-treated platelets in an artificial medium. According to Packham, *Thromb. Haemostas.*, 50:610-619 (1983), the responses of human platelets in such a medium differ from those in a medium in which a physiological concentration of ionized calcium is present. Thus, according to Packham, many studies of platelet function inhibitors have actually been studies of the inhibition of an artificial stimulation of the arachidonate pathway caused by close platelet contact in a medium with a low concentration of ionized calcium. Drawing conclusions from the studies on PPACK's ability to inhibit in vitro platelet aggregation is therefore difficult.

To date there has been no study of PPACK's effects on platelet aggregation in vivo or its ability to inhibit arterial thrombosis. This is not surprising in view of the above discussed teachings that agents such a heparin, which contravene not only thrombin's enzymatic activity but also its ability to stimulate platelet aggregation, are not effective in preventing arterial thrombosis.

BRIEF SUMMARY OF THE INVENTION

The present invention contemplates a method of inhibiting platelet dependent arterial thrombosis in a patient which method comprises administering to the patient a therapeutically effective amount of a Formula (1) peptide.

In another embodiment, the present invention contemplates a method of inhibiting posttherapeutic arterial restenosis in a patent which comprises administering the patient a therapeutically effective amount of a Formula (1) peptide, subjecting the patient to a therapeutic procedure for increasing the blood flow channel diameter in a stenosed artery to produce a treated artery, and circulating arterial blood of the patient through the treated artery.

Also contemplated by the present invention is a method of inhibiting platelet deposition on a prosthetic surface in a patient which method comprises administering to said patient a therapeutically effective amount of a Formula (1) peptide, and circulating arterial blood of the patient past a prosthetic surface.

BRIEF DESCRIPTION OF THE DRAWINGS

In the drawings forming a portion of this disclosure:

FIG. 3 contains 2 panels illustrating a study comparing the ability of PPACK versus heparin to inhibit platelet deposition on arterial grafts in baboons.

Figure 1:
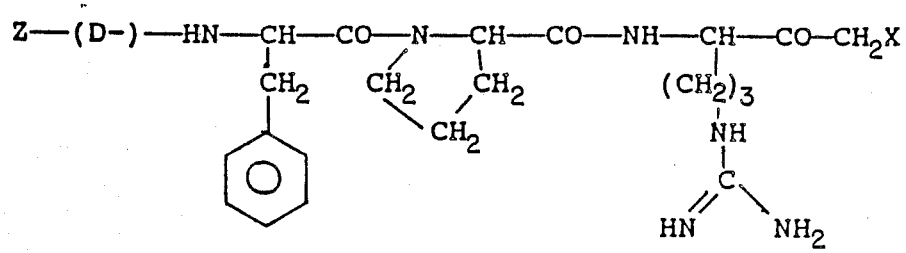
FIG. 1 illustrates Formula (1), a Formula representing a halogen-methyl ketone-containing peptide wherein X is a halogen atom, preferably chlorine or bromine, and Z is hydrogen or $C_1$-$C_6$ acyl, preferably hydrogen. The symbol (D-) indicates that the phenylalanine residue is dextrorotatory, the proline and arginine residue both having levorotary configurations.

In these studies autologous platelets were labeled with $^{111}$In-oxide. Then 5 cm segments of knitted Dacron vascular graft of 4.0 mm internal diameter (a gift from U.S. Catheter, Inc.) were inserted as extension pieces into a chronic exteriorized femoral arteriovenous silastic shunt. Blood flow through the shunt was measured using cuff Doppler transducer probe and average $175\pm16$ ml/min. $^{111}$In-platelet depositions onto vascular grafts was measured by gamma camera imaging (Dyna Camera, Picker Corporation) coupled with an image analysis system (Medical Date Systems A$_3$, Medtronic). The results were expressed as total platelets deposited by dividing the deposited platelet radioactivity by the circulating blood radioactivity per ml, and multiplying by the circulating platelet count per ml. The number of determinations is indicated in parentheses and the vertical bars denote means $\pm$ one standard deviation.

Panel A illustrates that in untreated control animals, $^{111}$In-platelets are rapidly deposited on Dacron vascular graft segments, reaching a plateau value of about $10^{10}$ platelets by 50 minutes. The grafts occur at 1.2 hr$\pm$0.2. Continuous intravenous infusions of PPACK at a rate of 100 nmol/kg/min for the 60 minute period designated by the horizontal hatched bar profoundly inhibited platelet deposition and prevented graft occlusion. Resumption of platelet dependent arterial thrombus formation occurs 30 minutes after discontinuing PPACK administration, as evidenced by the increase of platelet deposition after about the 90 minute position of the abscissa.

Panel B illustrates that administration of 100 units (U) of heparin per kilogram (kg) body weight to the baboon (a dose that produced a 3-fold prolongation in whole blood clotting time) did not significantly reduce platelet deposition onto the graft over the 60 minute exposure period. Panel B also illustrates that administration of 1000 U/kg to the baboon only partially inhibited platelet depositions on the grafts.

FIG. 4 contains two panels illustrating ability of PPACK to inhibit arterial restenosis ($^{111}$In-platelet deposition) at a carotid endarterectomy site. The vertical bars denote means $\pm$ one standard deviation. In untreated control studies (●), acute platelet deposition during the 90 minutes following initiation of arterial circulation through the treated artery is shown in panel A. Because the values shown in panel A are corrected for tissue attenuation using an implanted standard, the results are expressed as the number of deposited platelets.

The results obtained when PPACK (0) was intravenously administered at a rate of 100 nmol/kg/min for one hour begun immediately prior to circulating arterial blood through the treated artery are also shown in panel A.

In panel B, $^{111}$In-platelet deposition at the endarterectomy site is expressed as the endarterectomy/blood ratio, obtained as described in Example 1. From panel B, it can be seen that there was minimal progressive accumulation of $^{111}$In-platelet activity under both control (●) and PPACK treatment (0) conditions.

Figure 5:
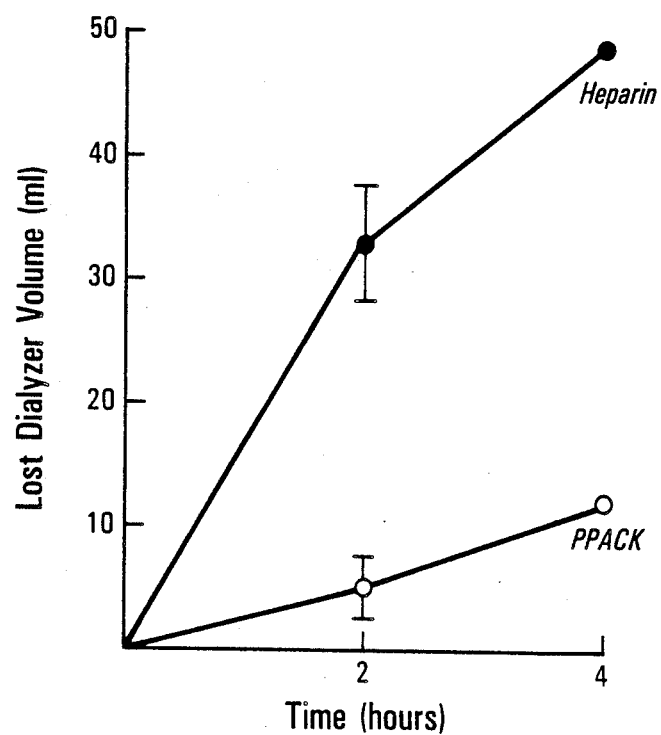

FIG. 5 illustrates the ability of PPACK (0), as compared to heparin (●), to inhibit volume loss in a hemodialyzer as a result of platelet deposition or the dialyzer prosthetic surface. The vertical bars denote means $\pm$ one standard deviation.

Figure 6:
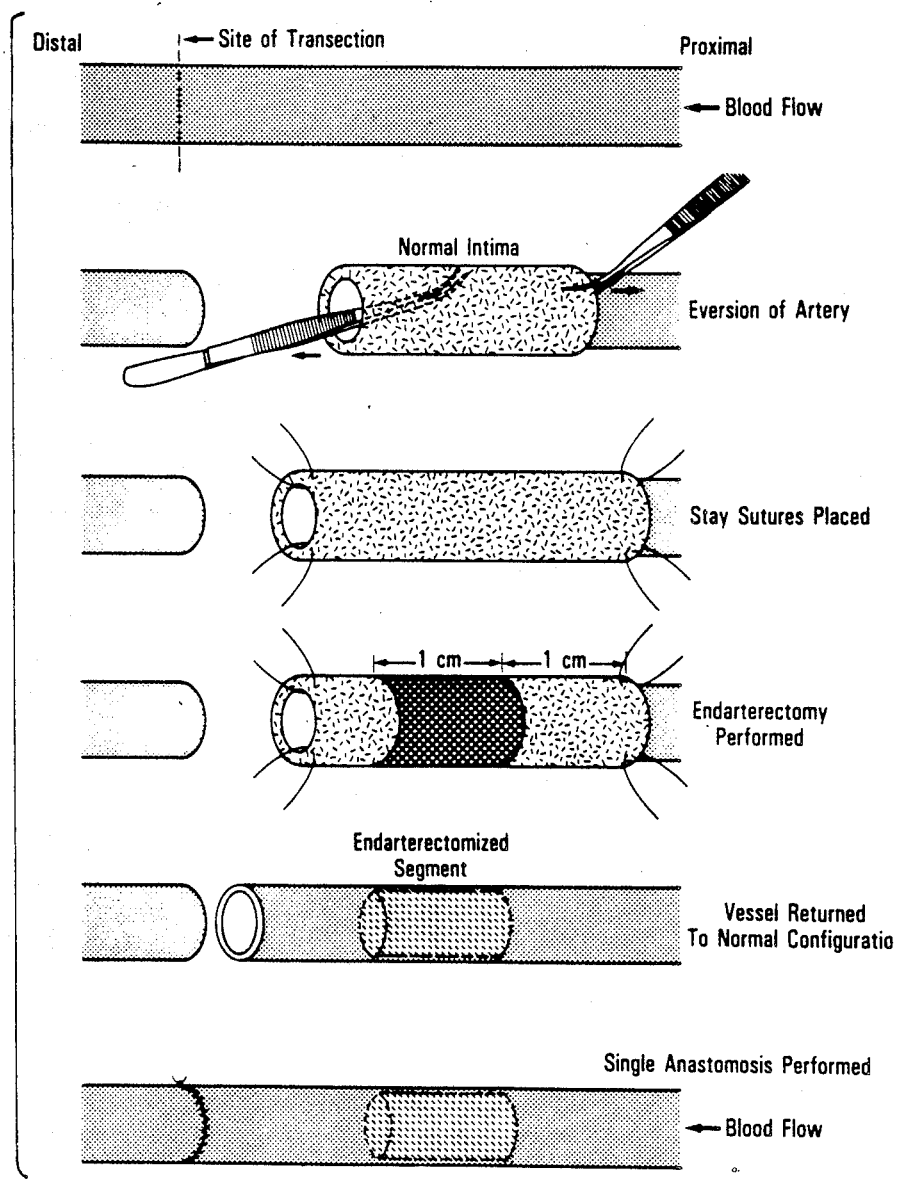

FIG. 6 illustrates a carotid endarterectomy procedure. The common carotid artery is clamped, then transected distally. The proximal segment is everted over curved forceps by applying countertraction. Stay sutures are placed and the endarterectomy is performed for a distance of 1 cm using microsurgical techniques. The vessel is returned to its usual configuration and an end-to-end anastomosis is performed. An intervening segment of normal intima is present between the endarterectomy site and the anastomosis.

Figure 7:
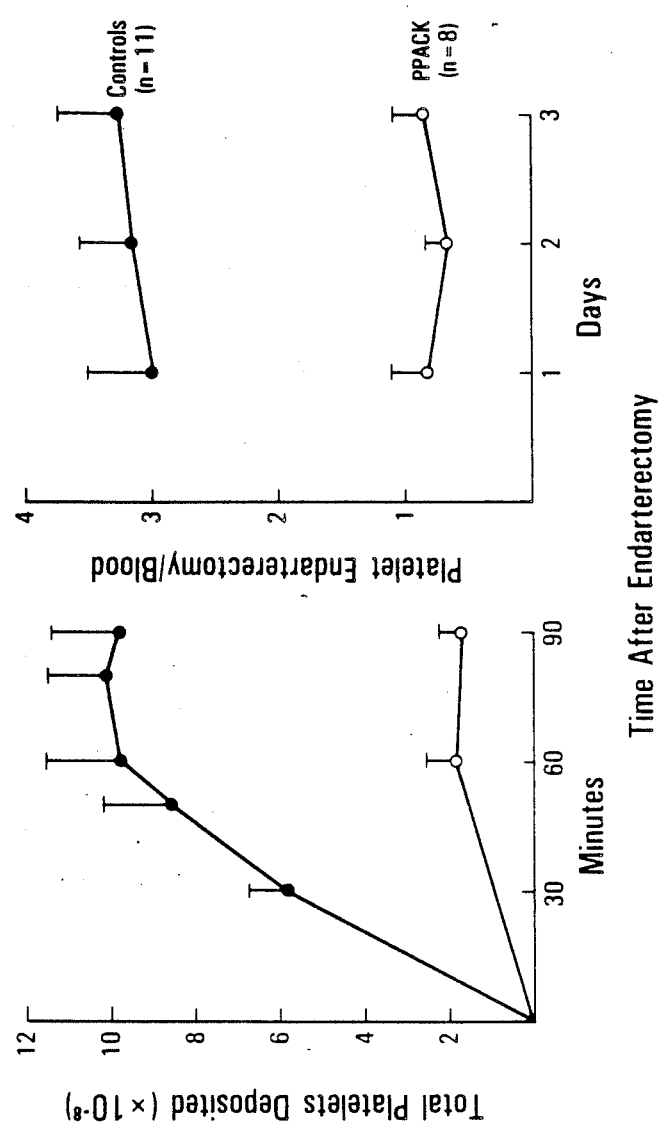

FIG. 7 contains two panels illustrating the ability of PPACK to inhibit platelet deposition at carotid endarterectomy sites. In untreated animals platelet deposition on carotid endartectomy sites increases rapidly reaching a plateau at 60-90 min. In animals treated with 100 nmol/kg intravenous infusion of PPACK for 60 min, platelet accumulation is greatly decreased. This effect is observed in the immediate postoperative previous (left) and throughout 3 days as evident from the platelet endarterectomy to blood ratio (right). The vertical bars denote a variance about the mean as $\pm$ one standard deviation. Comparison between the control and treated groups were performed by a two-tailed Student's t test.

Figure 8:
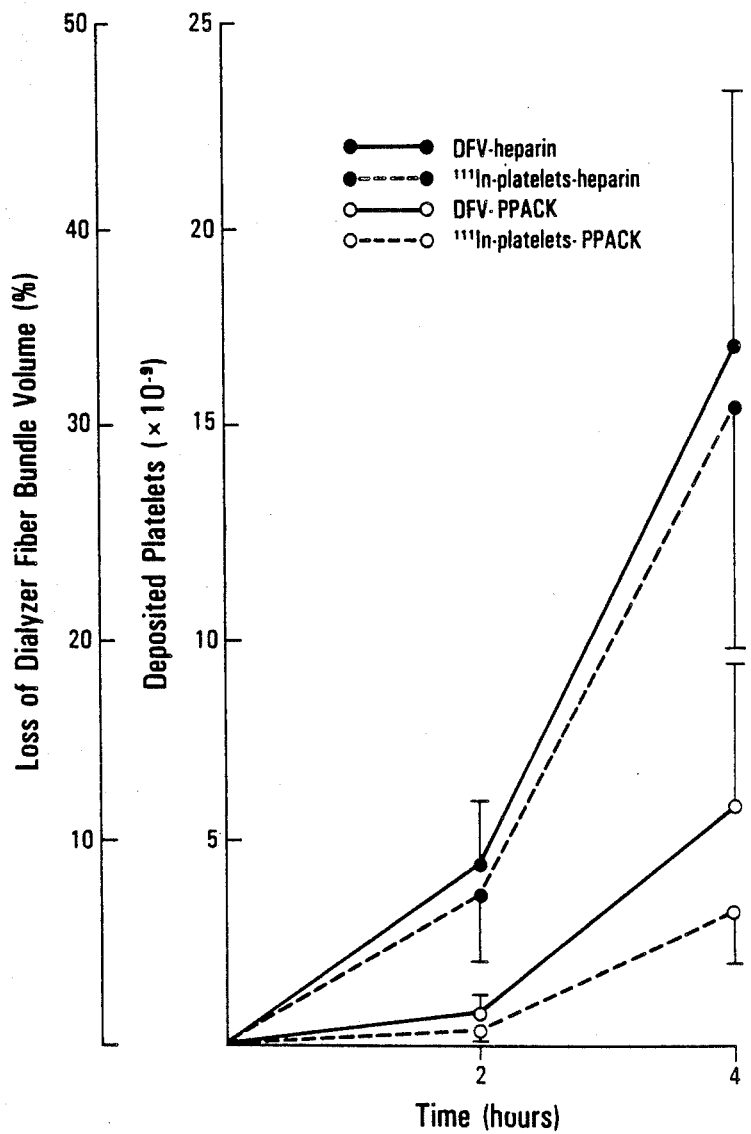

FIG. 8, as in FIG. 5 illustrates the ability of PPACK, as compared to heparin, to inhibit volume loss and $^{111}$In-platelet deposition within a fiber bundle (hemodialyzer) as an independent measure of the thrombus formation in the dialyzer after each use. Heparin-treated animals had significant and progressive losses of DFV and reciprocal increases in platelet accumulation within the fiber bundle at all times tested. By contrast, the PPACK-treatment preserved DFV with a marked reduction of platelet accumulation in the dialyzers.

DETAILED DESCRIPTION OF THE INVENTION

A. Definitions

"Angioplasty" refers to surgical reconstruction of narrowed (stenosed) arterial blood vessels. "Percutaneous transluminal angioplasty" is dilation of an arterial blood vessel by means of a balloon catheter inserted through the skin and into the chosen vessel and then passed through the lumen of the vessel to the site of the stenotic lesion, where the balloon is inflated to flatten plaque against the artery wall and thereby re-establish the flow channel in the diseased artery.

"Anticoagulant" refers to an agent that interrupts coagulation and thereby inhibits fibrin formation.

"Arterial lesion" refers to a thrombogenic surface to which arterial blood is exposed during circulation. Typical arterial lesions are de-endothelialized areas of an arterial wall, non-endothelialized prosthetic devices, and the like.

"Arterial prosthetic device" refers to a biologic or synthetic vascular prosthesis that is inserted into the vasculature so as to receive and transport arterial blood.

"Coagulation" refers to the sequential process in which the multiple coagulation factors of the blood interact resulting in the formation of fibrin.

"Endarterectomy" refers to excision of thickened, atheromatous tunica intima of an artery. A "gas endarterectomy" refers to an endarterectomy performed by utilizing high-pressure carbon dioxide to remove plaque deposits from the coronary blood vessels in the treatment of atherosclerosis. A "laser endarterectomy" refers to an endarterectomy performed by utilizing a catheter-directed laser to remove atherosclerotic plaques.

"Formula (1) peptide" in its various grammatical forms refers to a peptide represented by Formula (1) as shown in FIG. 1 and the hydrohalic addition products thereof.

B. Therapeutic Methods

The present invention contemplates new uses for a halogen-methyl ketone-containing peptide represented by Formula (1) as shown in FIG. 1, wherein Z is hydrogen or a $C_1$–$C_6$ acyl; X is a halogen atom; and the hydrohalic acid addition products thereof.

Figure 2:
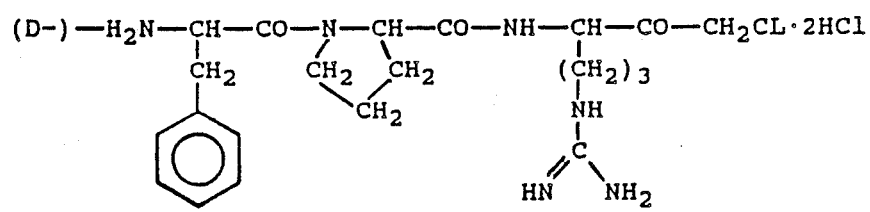
FIG. 2 illustrates Formula (2), the formula for PPACK, a preferred halogen-methyl ketone-containing peptide of Formula (1) wherein X is chlorine and Z is hydrogen.

A preferred halogen-methyl ketone-containing peptide is represented by Formula (2), as shown in FIG. 2, wherein Z is hydrogen and X is chlorine, and is designated herein as PPACK.

Halogen atoms preferably include chlorine, bromine or iodine.

Synthesis of a halogen-methyl ketone-containing peptide represented by Formula (1) and its use to contravene the enzymatic activity of thrombin are described in U.S. Pat. No. 4,318,904, Mar. 9, 1982, Shaw et al., whose disclosures are herein incorporated by reference.

The new uses for a peptide represented by a Formula (1) peptide were born out of the discovery that the peptide significantly inhibits platelet deposition on arterial lesions and thereby reduces the risk of platelet dependent arterial thrombosis.

Thus, the present invention contemplates a method of inhibiting platelet dependent arterial thrombosis in a patient which comprises administering to the patient a therapeutically effective amount of a Formula (1) peptide, preferably PPACK.

The phrase "therapeutically effective amount" when used in relation to a Formula (1) peptide, refers to an amount of peptide sufficient to increase the subject's thrombin time by at least about 2 fold, preferably at least about 5 fold and more prefer about least about 10 fold. In preferred embodiments of the present invention, a Formula (1) peptide is administered in an amount sufficient to achieve a peptide concentration in the plasma of at least about 0.2 micrograms per milliliter (ug/ml), preferably at least about 1 ug/ml and more preferably at least about 10 ug/ml. Typically administration of a therapeutically effective amount of Formula (1) peptide in a peptide concentration in the plasma in the range of about 0.2 ug/ml to about 10 ug/ml, preferably about 0.5 ug/ml to about 5 ug/ml, and more preferably about 1 ug/ml to about 2 ug/ml. That is, circulating blood containing a Formula (1) peptide at the above plasma concentration provides a method for inhibiting platelet dependent arterial thrombosis.

Methods for determining the concentration of a Formula (1) peptide in the plasma are well known in the art, a preferred method being that described by Collen et al., *J. Lab. Clin. Med.*, 99:76–83 (1982), whose disclosures are incorporated herein by reference.

Methods for diagnosing the presence of platelet dependent arterial thrombosis in a patient (human subject) are well known in the art. Those methods include contrast angiography, arteriography, computerized axial tomography (CAT) scanning, in vivo imaging using radionuclide-labeled platelets, location using two-dimensional Doppler devices, and the like. Specific diseases in which platelet dependent arterial thrombosis plays a role are also well known in the art and include cerebrovascular atherosclerotic disease, as evidenced by stroke or transient cerebral ischemia, coronary atherosclerotic disease, as evidenced by cardiac ischemia, unstable angina or acute myocardial infarction, peripheral arterial occlusive disease as evidence by distal ischemia, and the like.

Patients in need of treatment for platelet dependent arterial thrombosis also include those subject to a medical (therapeutic) procedure performed to improve blood flow through a stenosed artery. For instance, many patients suffer posttherapeutic restenosis due to platelet dependent thrombosis induced by an arterial lesion uncovered or created during a therapeutic procedure performed to remove an occlusive entity such as an arterial ulcer, atherosclerotic plaque arterial thrombus and the like.

Thus, the present invention contemplates a method of inhibiting post-therapeutic arterial restenosis in a patient which method comprises:

(a) Administering to the patient a therapeutically effective amount of a Formula (1) peptide, preferably PPACK.

(b) Subjecting the patient to a medical procedure for increasing the blood flow channel diameter in a stenosed artery and thereby produce a treated artery. Medical procedures for increasing the blood flow channel diameter of a stenosed artery are well known in the art and include surgical procedures (manual or operative remedial methods performed by manipulation or intervention with an instrument or device) and drug therapies. For instance, surgical procedures performed to improve the blood flow capacity of a stenosed artery include endarterectomy, particularly gas or laser endarterectomy, angioplasty, arterial vascular prosthesis insertion, and the like.

Medical procedures for increasing the blood flow capacity of a stenosed artery also include administering a therapeutically effective amount of a thrombolytic agent to the patient. Thrombolytic agents and their use are also well known in the art. Commercially available thrombolytic agents include streptokinase, urokinase and tissue plasminogen activator (tPA).

(c) Arterial blood of the patient is circulated through the treated artery.

In preferred methods for treating posttherapeutic restenosis, Formula (1) peptide administration according to (a) is performed prior to exposing circulating arterial blood to the treated artery according to (c). Preferably, (c) is performed subsequent to (a) but while the plasma concentration of a Formula (1) peptide administered according to (a) is at least about 0.2 ug/ml, preferably at least about 1 ug/ml and more preferably at least about 10 ug/ml. In other embodiments, (c) is performed within about 90 minutes, preferably within about 15 minutes and more preferably within about 5 minutes of performing (a). However, methods wherein (a) and (c) are performed substantially simultaneously (concurrently), and when (c) is performed prior to (a), are also contemplated.

Patients in need of treatment for arterial thrombosis further include those subject to having their circulating arterial blood exposed to a thrombogenic surface. Exposure of the arterial circulation to a thrombogenic surface typically occurs in patients in which an arterial prosthetic device has been operatively inserted. Thus, the present invention contemplates a method of inhibiting platelet deposition of an arterial prosthetic surface in a patient which method comprises:

(a) Administering to the patient a therapeutically effective amount of a Formula (1) peptide, preferably PPACK.

(b) Arterial blood of the patient is circulated past a prosthetic surface.

Arterial prosthetic devices having surfaces exposed to arterial blood when operatively inserted into a patient's circulation are well known in the art. See, "Biologic and Synthetic Vascular Prostheses," J. Stanley, ed., Grune and Stratton, N.Y. (1982). Exemplary biological arterial prosthesis include, autogenous arterial grafts, particularly autogenous saphenous vein arterial grafts, dialdehyde starch-tanned bovine heterografts, human umbilical vein grafts and the like. Synthetic arterial prothesis are also well known in the art and include Dacron grafts, expanded polytetrafluoroethylene grafts such as those described in U.S. Pat. No. 3,962,153, hydrophobic polymer-lined grafts such as those described in the U.S. Pat. No. 4,687,482, and the like.

Exemplary arterial prosthetic surfaces are arterial stens, A-V shunts, and the like. A-V shunts are typically sections of non-endothelialized tubing, usually constructed of a polymeric material, that are used to transport arterial blood in a vein, either directly or first through and ex vivo therapeutic device. Exemplary ex vivo therapeutic devices include cardiopulmonary assist devices, and the like. The use of ex vivo therapeutic devices is well known in the art.

In preferred methods for inhibiting platelet deposition on a prosthetic surface, Formula (1) peptide administration according to (a) is performed prior to circulating the patient's arterial blood past a prosthetic surface according to (b). Preferably, (b) is preformed subsequent to (a), but while the plasma concentration of a peptide administered according to (a) is at least about 0.2 ug/ml, preferably at least about 1 ug/ml and more preferably at least about 10 ug/ml. In other embodiments, (b) is performed within about 90 minutes, preferably within about 15 minutes and more preferably within about 5 minutes of performing (a). However, methods wherein (a) and (b) are performed substantially simultaneously, and wherein (b) is performed prior to (a), are also contemplated.

A peptide according to Formula (1) or a hydrohalic addition product thereof is typically administered as a pharmaceutical composition in the form of a solution or suspension, however, as is well know, peptides can also be Formulated for therapeutic administration as tablets, pills, capsules, sustained release formulation or powders. In any case, the administered composition contains about 0.10% to about 99% of a Formula (1) peptide, preferably 10%–90% and more preferably 25%–75%.

The preparation or therapeutic compositions which contain peptides as active ingredients is well understood in the art. Typically, such compositions are prepared as injectables, either as liquid solutions or suspensions, however, solid forms suitable for solution in, or suspension in, liquid prior to injection can also be prepared. The preparation can also be emulsified. The active therapeutic ingredient is often mixed with inorganic and/or organic excipients which are pharmaceutically acceptable and compatible with the active ingredient (peptide). Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

A therapeutic composition useful in the practice of the present invention can contain a Formula (1) peptide Formulated into the therapeutic composition as a neutralized pharmaceutically acceptable salt form. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and like. Salts formed with the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The therapeutic peptide-containing composition is conventionally administered intravenously, as by injection of a unit dose, for example. The term "unit dose" when used in reference to a therapeutic composition used in the present invention refers to physically discrete units suitable as unitary dosages for humans, each unit containing a predetermined quantity of active material calculated to produce the desired therapeutic effect in association with the required excipient.

The composition is administered in a manner compatible with the dosage formulation, and in a therapeutically effective amount. The quantity to be administered depends on the subject to be treated, capacity of the subject's blood hemostatic system to utilize the active ingredient, the degree of platelet aggregation inhibition desired. Precise amount of active ingredient required to be administered depends on the judgement of the practitioner and are peculiar to each individual. However, suitable dosage ranges are of the order of one to hundreds of nanomoles of Formula (1) peptide per kilogram body weight per minute and depend on the route of administration.

In another embodiment, the present invention contemplates a thrombo-resistant vascular prosthesis comprised of an elongated tabular segment that has a substantially non-compliant, hollow body portion open at both ends. The hollow body portion has a luminal (circulating blood-contacting) surface that defines a confined-flow channel. A Formula (1) peptide is removably affixed to the luminal surface.

By "removably affixed" is meant that a Formula (1) peptide is affixed to the luminal surface of the prosthesis so as to be capable of dissolving into the plasma upon contact with blood circulating through the confined flow channel. Removable affixation is accomplished by well known methods including deposition by adsorption of a solid or liquid form of a Formula (1) peptide onto the luminal surface. When a substantially pure form (at least about 99% pure) of a peptide is linked to the surface it will very rapidly dissolve upon contact with the circulating blood to provide a localized peptide concentration of the prosthetic luminal surface about equal to the peptide's solubility in plasma.

In preferred embodiments, a Formula (1) peptide removably affixed to the luminal surface of the prosthetic device is present as part of a slow release formulation. A typical slow release formulation includes a Formula (1) peptide admixed with a pharmaceutically acceptable, biodegradable excipient. Pharmaceutically acceptable, biodegradable excipients suitable for use in slow release formulations are well known and include polymers (e.g., polyethylene glycol), polyamino acids (e.g., polyglycolic acid), and the like. When a slow release formulation containing a Formula (1) peptide is removably affixed to the luminal surface, the local concentration of a peptide in the blood (i.e., the peptide concentration at the blood-luminal surface interface) will be proportional to the excipient dissolution rate. While the ratio of peptide to excipient depends, as is well known in the art, on the choice of excipient and blood flow conditions through the prosthetic flow channel, therapeutically effective amounts of a Formula (1) peptide can be delivered to blood contacting the luminal surface for a period of from hours to days when a slow release formulation is used.

The vascular prosthesis of the present invention, in its preferred embodiment, is substantially non-compliant. As used herein the expression "non-compliant" means showing less than 10 percent expansion of the inner diameter between systole and diastole under normal arterial pressures (less than 250 mmHg). The external surface of the vascular prosthesis permits tissue anchoring upon implantation in a human or other mammals, as is common for currently commercially available prostheses.

The tubular segment of the vascular prosthesis may be constructed of materials that exhibit the requisite strength, durability and suturability. Commercially available materials suitable for us in fabricating the prosthesis or graft include a polyester such as Dacron (C. R. Bard, Inc., Billerica, Mass.) and a polyfluorocarbon such as Teflon (Gore-Tex) (W. L. Gore, Flagstaff, Ariz.).

In preferred embodiments the luminal surface is comprised of polymers that form a relatively smooth, non-polar and hydrophobic surface. Such materials and either use in forming a portion of a luminal surface as described in U.S. Pat. No. 4,687,482 to Hanson, whose disclosures are incorporated herein by reference.

A thrombo-resistant vascular prosthesis of the present invention is produced by a method comprising removably affixing a Formula (1) peptide onto the luminal surface of the prosthesis. Thus, removably affixing a Formula (1) peptide to the luminal surface of a vascular prosthetic device is a method for improving the thrombo-resistance of that device.

EXAMPLES

The following examples are intended to illustrate, but not limit, the present invention.

1. In Vivo Inhibition of Platelet Deposition on a Synthetic Arterial Prosthetic Device To qualify the rate of acute arterial thrombus formation in vivo in a manner that is free of uncontrolled variables, a primate model of vascular graft thrombosis was used. Baboons were chosen for these studies because they appear to have thrombotic processes similar to humans. The extent of acute thrombus formation was measured in real time by scintillation camera imaging of autologous $^{111}$Indium-labeled platelet deposition onto segments of small caliber Dacron vascular grafts as described in Hanson et al., *Arterio*, 5:595–603 (1985).

Briefly, a chronic arteriovenous shunt was surgically implanted between the femoral artery vein (A-V shunt) of a normal, 10–12 kilogram male baboon (*Papio anubis*). The permanent shunt system consisted of two 25 centimeter (cm) lengths of silastic tubing having an inner diameter (i.d.) of 3 millimeters (mm; Dow Corning Corp., Midland, Mich.) connected to 13- and 15- gauge Teflon vessel tips (Lifemed, Venitron Corp., Compton, Calif.). In addition, the two Silastic lengths were fixed with Dacron sewing cuffs (Dupont, E. I. de Nemours and Co., Wilmington, Del.) at skin exit sites. Blood flow was established by connecting the two Silastic shunt segments with a 1 cm length of blunt-edge Teflon tubing (2.8 mm i.d.). In all studies, Dacron vascular grafts were subsequently operatively linked to the animal by interposing them between the segments of the permanent Silastic A-V shunt.

Model synthetic vascular prosthesis were prepared for use in the A-V shunt system by rendering a 10 cm length of uncrimped knitted Dacron graft material (Savage external velour, mean porosity 2000 to 2200 ml/H$_2$O/min at 120 mm Hg, 4.0 mm i.d.) impervious to blood leakage in the following manner.

First, a 4.0 mm Teflon rod (that had been thoroughly cleaned using a mild soap solution, then ethanol, and finally by rinsing with sterilized distilled water) was inserted through the graft. The graft was then externally wrapped with a 5×10 cm sheet of Parafilm and placed inside a 10 cm length of 6.3 mm i.d. "heat shrink" Teflon tubing (Small Parts Inc., Miami, Fla.).

The Teflon tubing containing the graft segment was gently heated over a low Bunsen flame until shrinkage to about 5.3 mm. had occurred, resulting in a compression of the Parafilm onto the external fabric interstices without modification of the liminal graft surface. Silicone rubber tubing, 10 cm×4.0 mm i.d., was transferred onto the Teflon rod and connected to both ends of the graft segment using Silastic Medical Grade Adhesive, silicone Type A. When the polymer had cured for 24 hours, the Teflon rod was carefully pulled from the tubing lumen. This procedure produced impervious grafts rigidly constrained to a linear geometry, and having an inner diameter of 4.0 mm. The resulting isodiametric flow channel was smooth in its transition from the Silastic to the graft surface without imperfections due to the coupling procedure. The graft was connected into the baboon shunt system using blunt-edge Teflon connectors.

Autologous baboon blood platelets were labeled with $^{111}$In-oxine according to the following procedures. Whole blood (100 ml) was collected directly into plastic bags (TA-3, Fenwal Labs, Deerfield, Ill.) containing 20 ml acid-citrate-dextrose anticoagulant (NIH Formula A). The blood was centrifuged in the bag at 300×g for 10 minutes. The supernatant platelet-rich plasma (PRP) was then transferred to a second bag and the pH adjusted to 6.5 by the addition of 0.15M citric acid (0.1 ml/10 ml PRP). The red blood cell fraction was returned to the donor mammal. The platelets were formed into a pellet by centrifugation of the PRP at 1300×g for 15 minutes. The supernatant platelet-poor plasma (PPP) was completely decanted and discarded.

To remove residual plasma proteins, the bag containing the platelet pellet was carefully washed once by overlaying with 30 ml of Ringer's citrate dextrose (RCD, pH 6.5) that was then decanted and discarded. The pellet was then gently resuspended in 5.0 ml RCD, and incubated for 30 minutes with 500–700- micro Ci $^{111}$In-oxine (Amersham Corp., Arlington, Heights, Ill.). Contaminating red cells were removed by a final slow centrifugation at 200×g for 5 minutes.

Labeling efficiency was determined by diluting 200 microliters of the labeled-platelet concentrate with 5.0 ml RCD, and comparing the activity in 0.5 ml of the diluted platelet suspension with the activity in 0.5 ml of cell-free supernatant following centrifugation at 3000×g for 30 minutes. A measured volume of labeled platelet suspension containing approximately 13 percent non-platelet bound isotope was then injected directly into the recipient mammals following the preparation of a 100 microliter standard. Additional washing procedures to remove non-platelet bound isotope were deemed undesirable since they may produce in vitro cell damage.

Circulating platelet $^{111}$In-activity was determined from 4 ml blood samples drawn prior to and following graft placement, and collected in 2 mg/ml (ethylenedinitrilo)-tetracetic acid (EDTA). One ml of each sample was used for platelet counting, and 1.0 ml was counted for whole blood $^{111}$In-activity. The remaining 2 ml were centrifuged at 3000×g for 30 minutes, and 1.0 ml of the supernatant (PPP) was counted for plasma $^{111}$In-activity. All blood and plasma samples were counted using a gamma spectrometer (Nuclear Chicago, Chicago, Ill.). Platelet counts were performed on whole blood using a electronic platelet counter (Clay Adams UF-100, Parsippany, N.J.).

Scintillation camera imaging of both gamma photon peaks of $^{111}$In (172 keV and 247 keV) has generally required high energy collimation to prevent image blurring, despite a decreased in both sensitivity and spatial resolution. Since platelet-specific activity was not a limiting factor in the present studies, a high sensitivity $^{99}$Tc collimator could be used with good resolution by imaging only the lower energy peak of $^{111}$In (172 keV peak and with a 5 percent energy window). Images of the Dacron grafts, including proximal distal Silastic segments, were acquired with a Picker DC 4/11 Dyna scintillation camera (Picker Corp., Northford, Conn.) and stored on and analyzed by a Medical Data System SIMUL computer (Medtronic, Ann Arbor, Mich.) interfaced the camera. This system permitted simultaneous acquisition and analysis of data in 64×64 word mode and was used to generate the data shown in FIG. 3. Immediately prior to imaging the graft segments ex vivo, 2 minute images were acquired of the 200 microliter sample of platelet concentrate (injection standard) and of 4.0 mm i.d.. Silastic tubing filled with autologous blood and having the same luminal volume as the graft segment (blood standard).

All standards and tubing were placed into a groove precisely machined into plexiglass to maintain a linear geometry that was positioned approximately 1 cm from the face of the collimator. The activities of the standards and 10 cm graft segments were counted in the same 3.1 cm×12.5 cm region of interest (10×40 pixels) and defined by image analysis software routines. From the time of graft placement, images were acquired continuously with date storage at 2 minute intervals. Deposited $^{111}$In-platelet activity was calculated by subtracting the blood standard activity from all dynamic study images.

Grafts were placed and imaged sequentially for several days following injection of a single preparation of $^{111}$In-platelets. Since circulating $^{111}$In-platelet activity was lost continuously through normal physiologic mechanisms, and acutely by serial graft placement, measurements of platelet accumulation were expressed as a graft/blood ratio, defined as the ratio of deposited graft activity divided by the whole blood (circulating) platelet activity within the graft lumen measured at the beginning of each evaluation. This measurement was chosen sine it is independent of the size of the mammal, the amount of isotope injected, or the extent to which the isotope may have decayed, Ritchie et al., *Am. J. Cardiol.*, 47:882 (1981); Callow et al., *Ann. Surg.*, 191:362 (1980). The graft/blood ratio, however, depends upon the timing or sequence of observations in platelet functional alterations occur as a result of aging in the circulation or repeated exposure to thrombogenic surfaces.

To determine the graft/blood ratio, the activity of blood within the graft lumen (1.26 ml) was determined by two separate methods. First, it was calculated directly after imaging the blood standard 1.57 ml. blood volume). In the second method, the activity per ml of blood present at the beginning of each experiment was calculated by imaging the injection standard prior to each experiment, multiplying this value by the CPM per ml of whole blood drawn at the time of the experiment (as determined using a gamma counter at some later time $t_1$), and dividing by injection standard activity (also measured in the gamma counter at $t_1$). All blood samples and standards were counted simultaneously at the end of each series of evaluations. In all calculations, radioactivity values refer to platelet activity only, with total blood and standard values having been corrected for the fraction of non-platelet isotope.

Total platelet deposition (labeled plus unlabeled cells) were estimated by multiplying the graft/blood ratio by the factor: graft blood volume (1.26 ml)×platelet concentration per ml of whole blood. This computation involved the assumption that the labeled and unlabeled platelet populations were equivalent with respect to graft deposition at all times. Values for total platelet deposition onto the vascular grafts as determined by the above method are shown in FIG. 3.

In untreated control animals, platelet deposition onto the vascular grafts reached a plateau value of $8.5 \times 10^9$ platelets at 60 minutes (FIG. 3), and the grafts occuled at 1.2±0.2 hours. In addition, as shown in Table 1, elevated plasma levels of the platelet-specific alpha-granule proteins, platelet factor 4 (PF4) and beta-thromboglobulin ($\beta$TG), and of fibrinopeptide A (FPA), the thrombin cleavage product of fibrinogen were observed during thrombus formation in these control studies.

TABLE 1

Effects of PPACK on Vascular Graft Thrombus Formation

| | Baseline | | PPACK-Treated | |
|---|---|---|---|---|
| | Pre-Graft | Graft | Pre-Graft | Graft |
| platelet count (× 10$^9$/L)[1] | 344 ± 68 | 290 ± 75 | 275 ± 56 | 269 ± 54 |
| 111In-platelets deposited (× 10$^9$) | — | 8.5 ± 1.0 | — | 0.4 ± 0.2 |
| plasma PF4 (ug/L)[2] | 9.2 ± 2.4 | 18.5 ± 1.7 | 7.1 ± 1.9 | 4.4 ± 0.2 |
| plasma BTG (ug/L)[2] | 6.0 ± 2.6 | 26.2 ± 1.2 | 8.0 ± 2.0 | 1.4 ± 0.2 |
| plasma FPA (nmol/L)[3] | 20.8 ± 2.7 | 27.2 ± 8.6 | 19.0 ± 4.7 | 2.0 ± 0.54 |

[1] Platelets, counted electronically in whole blood (J. T. Baker. Model 810 Analyzer, Allentown, PA) were decreased in the circulation due to platelet formation during vascular graft thrombus formation.
[2] Plasma PF4 and B-TG were measured by radioimmunoassay on blood samples collected and processed as described by Hanson et al., Arterio., 5:595–603 (1985). Elevation of these platelet-specific proteins in plasma reflected release from those platelets utilized in thrombus formation.
[3] FPA levels, measured by radioimmunoassay, Hanson et al., ibid., were also increased and represent thrombin-cleavage product of fibrinogen during thrombus formation in graft thrombus.

Conventional doses of heparin (100 units/kg given as a bolus prior to exposing arterial blood to the graft) had no effect on graft platelet deposition (FIG. 3B; $p>0.5$), although a tenfold increase in heparin dose was partially effective (FIG. 3B). It should also be noted that neither aspirin (32.5 mg/kg/day given orally 2 hours prior to graft placement) not aspirin combined with heparin (100 units/kg) affected vascular graft $^{111}$In-platelet deposition in similarly performed previous studies. See Harker et al., In "Vascular Diseases: Current Research and Clinical Applications", Strandness et al., (eds) Orlando, Grune & Stratton, pp. 271-283 (1987). Thus, in control animals the vascular graft was highly thrombogenic and resisted conventional antithrombotic therapies designed to inhibit fibrin formation (heparin treatment), platelet function (aspirin treatment) or both (aspirin and heparin treatment).

In contrast, intravenous infusion of PPACK at 100 nmol/kg/min. a rate that achieved a PPACK concentration in the plasma of about 1-2 ug/ml, abolished $^{111}$In-platelet deposition and prevented graft occlusion (FIG. 3A). As shown in Table 2, PPACK also abolished hemostatic platelet plug formation (bleeding times were prolonged to >30 min., $p<10^{-5}$ compared with controls) and thrombin-induced blood clotting (thrombin times were >10 min., $p<10^{-5}$ compared with controls).

TABLE 2

Effect of PPACK om Hemostatic Function

| Platelets[1] | Baseline | During PPACK (100 nmol/kg/min) | After PPACK (15 min) |
|---|---|---|---|
| platelet count ($\times 10^9$/L) | 290 ± 75 | 275 ± 56 | 269 ± 54 |
| bleeding time (min) | 5.4 ± 0.3 | >30 | 5.9 ± 2.6 |
| aggregation (ED$_{50}$): | | | |
| ADP (uM) | 7.1 ± 0.8 | 2.3 ± 0.3 | — |
| collagen (ug/ml) | 4.2 ± 0.4 | 2.6 ± 0.3 | — |
| thrombin (U/ml) | 0.1 | >20 | |
| Coagulation | | | |
| fibrinogen (gm/L) | 3.67 ± 0.33 | 3.80 ± 0.33 | 3.75 ± 0.35 |
| thrombin time (sec) | 21 ± 3 | >600 | 19 ± 1 |
| Fibinolysis | | | |
| plasminogen (mg/L) | 163 ± 13 | 163 ± 8 | 174 ± 7 |
| D-dimer (mg/L) | 0.45 ± 0.10 | 0.49 ± 0.08 | 0.53 ± 0.13 |

[1]Platelet hemostatic function was assessed with respect to platelet count, platelet plug forming capability (template bleeding time), and platelet aggregation. Platelet aggregation was measured by recording the light transmission through stirred suspensions of citrated platelet-rich plasma. The results are expressed as that concentration of agonist (ADP, collagen and thrombin) required to produce half maximal aggregation. Results are expressed as means ± one standard deviation.

Additionally, there was no detectable release of PF4 or βTG from platelets or FPA into plasma during PPACK administration (Table 1).

The results of in vivo dose-response studies, shown in Table 3 demonstrate an unexpected concordance in prolongation of thrombin-induced blood clotting and of bleeding times with maximal effects observed at a PPACK plasma concentration of about 1-2 ug/ml, achieved by infusion at a rate of 100 nmol/kg/min for about 15 minutes.

TABLE 3

Dose-Response Effect of PPACK

| Dose of PPACK[1] (nmol/kg/min) | Bleeding Time (min) | Thrombin Time (sec) |
|---|---|---|
| 0 | 5.4 ± 0.3 | 17 ± 3 |
| 15 | 7.6 ± 1.6 | 19 ± 3 |
| 30 | 9.5 ± 4.2 | 22 ± 2 |
| 60 | 26.6 ± 3.4 | 279 ± 132 |
| 100 | >30 | >600 |

[1]In five different animals PPACK was infused intravenously according to the indicated dose-escalating regimen. After continuous infusion of a given dose for 15 minutes (min.), the template bleeding time measurement was begun and blood was drawn for thrombin time determinations. Escalation to the next dose was undertaken only after the bleeding time measurement had been completed. The results are expressed as means ± one standard deviation.

When PPACK was added to baboon plasma in vitro, thrombin times prolonged sharply at concentrations of 6 uM/1 or greater, consonant with the infusion data (Table 3). No effect on heart rate or blood pressure occurred during therapy. After discontinuing PPACK infusion, $^{111}$In-platelet graft deposition normalized over 30 min., as shown in FIG. 3A, and bleeding times and thrombin times largely normalized within 15 min., as shown in Table 2.

Whereas thrombin-induced platelet aggregation was abolished when PPACK was present at concentrations of 3.2±0.1 mh=g/L or greater (Table 2), platelet aggregation induced by collagen or ADP was not inhibited by PPACK (Table 2). Thus, the intrinsic reactivity of platelets was unaffected.

2. In Vivo Inhibition of Platelet Deposition and Arterial Restonosis

A. The ability of PPACK to inhibit arterial restonosis was examined in a baboon model of in vivo arterial graft insertion and endarterectomy. For graft insertion, a small vascular prothesis in the form of a 3 cm long Goretex graft (4 mm i.d.,), was operatively inserted into the carotid artery of a male baboon. Immediately prior to circulating arterial blood through the graft (past the prosthetic surface), and for a time period of about 1 hour thereafter, PPACK was intravenously administered to the baboon at a rate of about 100 nmol/kg/min. A control animal received no PPACK treatment. $^{111}$In-Platelet deposition was monitored upon reconstitution of arterial blood flow as described in Example 1.

For endarterectomy, baboon carotid arteries were endarterectomized according to standard surgical procedures. Immediately prior to circulating blood through the endarterectomized (treated) artery, and for a time period of about 1 hour thereafter, PPACK was administered intravenously to the baboon at a rate of about 100 nmol/kg/min. A control animal received no PPACK.

The results of both studies were comparable. Data from the endarterectomy study are shown in FIG. 4 and indicate that platelet deposition (restenosis) was inhibited 90%-95% in the animal receiving PPACK administration as compared to the control animal.

B. In another study of carotid endarterectomy, 14 baboons weighing 8 to 11 kg (10 males and 4 females) were endarterectomized by standard surgical procedures as described herein.

The animals were administered atropine (0.04 mg/kg intramuscularly) as a pre-anesthetic agent and then anesthetized using ketamine (10 mg/kg intramuscularly) for induction and maintenance with halothane (1% in oxygen) by endotracheal tube. Through a midline neck incision, the common carotid artery was dissected free of surrounding tissues from the clavicle proximally to the carotid bifurcation distally. The common carotid artery was cross-clamped using atraumatic vascular clamps placed at each end of the exposed vessel three minutes after a bolus injection of heparin sulfate (100 units per kilogram (U)/(kg) intravenously) and divided 1 cm proximal to the distal cross clamp (FIG. 6). The proximal arterial segment was then everted over curved forceps. The forceps were inserted through the cut end of the vessel, a full thickness purchase of the arterial wall from the intraluminal side was then obtained, and the vessel was everted by applying countertraction on the divided end of the vessel in the proximal direction. After maximal exposure was obtained, one pair of polypropylene stay sutures (7-0) was placed on either side proximally and a second pair distally in the lumen-exposed segment. The endarterectomy was then performed beginning 1 cm from the divided end of the everted vessel segment and continued for a distance of 1 cm. This procedure involved mechanical removal of the normal intima and a partial thickness of media using forceps and a surgical microscope (32 X magnification, Zeiss operating microscope, West Germany). Following endarterectomy, the vessel was returned to its normal configuration, and an end-to-end anastomosis was performed with 7-0 polypropylene suture under 2½fold magnification. In the treated animals intravenous PPACK infusion was initiated 5 min prior to restoration of flow in the operated carotid artery. Patency was assessed using a 5-MHz pencil Doppler probe (Parks Electronics Laboratory, Beaverton, Oreg.) both proximal and distal to the endarterectomy site and the anastomosis. An $^{111}$In-source was implanted as an internal standard (see below). The wound was closed with interrupted sutures and scintillation camera images were performed immediately. The animals tolerated the procedure well. The estimate of blood loss was approximately 25 ml.

Autologous baboon blood platelets were labeled with 800–1000 μCi (1Ci=37GBg) $^{111}$In-oxide, as previously described in Example 1, and were injected prior to the surgical procedure.

A medium energy collimator was used with good resolution by imaging both the upper and lower energy peaks of $^{111}$Indium. Images of the carotid arteries were acquired with a Picker DC 4/11 Dyna scintillation camera (Picker Corp., North-ford, Conn.) and sorted and analyzed by a Medical Data System A$^3$ computer (Medtronic, Ann Arbor, Mich.) interfaced with the camera. Images were also acquired of a 5 ml sample of whole blood (blood standard).

For purposes of calibration, a small $^{111}$In-radioisotope source (approximately 5 μCi) was sealed at the end of 0.6 mm i.d. polyethylene tubing (PE-50, Clay Adams Incorporated, New York N.Y.) and placed at the time of surgery adjacent to the common carotid artery in the same tissue plane as the endarterectomy site. After acquiring the initial 5 min image (see below), the $^{111}$In-source was withdrawn and recounted. The ratio of $^{111}$In activity of the internal standard when implanted in the wound and after removal give a direct measure of the attenuating effect of the intervening tissues on the $^{111}$In activity deposited at the endarterectomy site. Hanson et al., Arteriosclerosis, 6:511–518 (1986). The activity of a 5 ml whole blood standard, internal calibration standard before and after removal from the would, endarterectomy sites and control contralateral arteries are counted in regions of interest as defined by image analysis software routines. Deposited $^{111}$In-platelet activity is calculated by subtracting the activity in the contralateral control artery region from study images, correcting for tissue attenuation, and expressing the results as platelets deposited using the whole blood standard.

As in Example 1, circulating $^{111}$In-platelet activity is lost continuously through normal physiologic mechanisms and measurements of platelet accumulation after the acute images can not be expressed in terms of total numbers. Data is taken at later time points and expressed as the endarterectomy to blood ratio, defined as the ratio of endarterectomy region activity minus the circulating blood platelet activity within the lumen of the contralateral unoperated control artery divided by the blood standard activity. This measurement is independent of the size of the animal, the amount of isotope injected or the extent to which the isotope may have decayed. In all calculations, radioactivity values refer to platelet activity only, with total blood and standard values having been corrected for the small fraction of non-platelet $^{111}$In activity. Hanson et al., J. Clin. Invest., 81:149–158 (1985).

Following unilateral carotid endarterectomy in each animal, 5-minute scintillation camera images were taken at 60 and 90 min. and 24, 48, and 72 hours after blood flow was reestablished. On postoperative day 1, prior to the 24-hour image, each baboon was anesthetized with ketamine hydrochloride (10 mg/kg), the wound was opened, and arterial patency was assessed using the pencil-probe Doppler. The wound was closed and imaging was performed.

Platelet counts and hematocrit determinations were performed preoperatively and daily for 2 days on whole blood collected in Na$_2$EDTA (2 mg/ml) using a Baker model 810 whole blood analyzer. The mean platelet count was $318\pm70\times10^3/\mu l$ in the control group and $296\pm53\times10^3/\mu l$ in the treated group.

Bleeding time measurements were performed in duplicate on the shaved volar surface of the forearm, using the standard template method as previously described for studies in baboons. Harker et al., Blood, 58:824–834 (1980).

Antithrombin activity levels of PPACK were measured in plasma prepared from blood collected in acid-citrate dextrose (ACD) obtained before infusion and at 30 and 60 minutes after the start of infusion and 30 minutes after the conclusion of therapy. Plasma antithrombin activity levels were assayed immediately, or flash frozen at $-70°$ C. for subsequent assay, using a standard curve for PPACK prepared in the animals own control pretreatment plasma.

The PPACK solution was dissolved in 0.15 M NaCl and sterilized by filtration. The PPACK solution was infused continuously for about 1 hour using a syringe pump (Harvard Apparatus Co., Cambridge, Mass.) at a rate of 100 nmol/kg/min.

The platelets were rapidly deposited at carotid endarterectomy sites in control animals, reaching a plateau within 60 min after reestablishing flow (FIG. 7). Thereafter the endarterectomy to blood ratio (EBR) remained elevated in the controls, increasing only minimally during the first three days from $3.03\pm0.51$ to $3.25\pm0.48$ (p=0.759; FIG. 7). In contrast, acute platelet deposition at 90 min after surgery on the endarterectomy sites was markedly decreased in animals treated with PPACK as compared to the control animals (1.59±0.36×10⁸ vs. 11.67±1.61×10⁸ platelets/cm, respectively; p<0.002) over the subsequent 3 days platelet deposition remained reduced when assessed as the ratio between net radioactivity in the endarterectomized region vs where blood activity in the controls respectively (EBR). On the day of operation, at 90 min. the ratio was 0.82±0.25 in PPACK animals and 3.03±0.51 in the control animals respectively. After 3 days the EBR ratio of 0.85±0.23 in PPACK animals compound with 3.25±0.48 in the control animals. All the vessels were patent in both groups at 24 control hours by Doppler scanning.

The scintillation camera images obtained at 90 minutes following the operation demonstrated focal accumulation of platelets at the endarterectomy sites in control animals. PPACK treatment resulted in a marked reduction of $^{111}$In-platelet activity at the endarterectomy sites.

Scanning electron microscopy of the untreated endarterectomized vascular surface 3 days after endarterectomy demonstrated acute platelet-thrombus formation. Visible platelet deposition at endarterectomy sites in animals receiving PPACK treatment was markedly reduced.

The plasma levels of PPACK were maintained constant during infusion but fell quickly after the infusion was discontinued (Table 4). PPACK increased template bleeding times before treatment from 5.6±0.8 minutes to >30 minutes in all animals during infusion. The bleeding times were normal 30 min after discontinuing the infusion of PPACK (6.2±1.3 minutes).

Platelet counts remained unchanged in the treated animals over the course of the study (296±53×10³/μl on day 3, p=0.725).

TABLE 4

| Plasma Levels of PPACK | |
|---|---|
| Baseline | — |
| 30 min after infusion | 3.72 ± 0.61 μg/ml |
| 60 min after infusion | 3.71 ≦ 0.47 μg/ml |
| 90 min after infusion | 1.12 ± 0.27 μg/ml |
| 24 min after infusion | — |

The results of this study show that intravenous administration of PPACK for about one hour permanently interrupts platelet deposition at sites of severe injury produced by surgical endarterectomy in the carotid arteries of baboons. These findings also indicate, as do those in Part A, that the one hour infusion of PPACK achieves significant inhibition of platelet deposition for at least 3 days.

Continuous administration of PPACK, as suggested by the art, is therefore not required to achieve significant late post-operative therapeutic affects.

The present invention thus provides a means for inhibiting platelet dependent arterial thrombosis associated with interventional vascular procedures such as angioplasty, endarterectomy, intravascular stent placement and small caliber vascular graft implantations in mammals.

3. Inhibition of Platelet Deposition On An Arterial Prosthetic Surface

A. The effect of PPACK using a hollow fiber (capillary) hemodialyzer as an exemplary ex vivo therapeutic device placed in chronic arterio-venous femoral shunts was chosen to demonstrate the anti-thrombotic effects on prosthetic surfaces.

A 0.8 m² cuprophane capillary flow dialyzer (Model 12.11; Travenol, Deerfield, Ill.) was inserted into a A-V shunt systems of 7 different male baboons as described in Example 1. PPACK was administered intravenously to the baboons at a rate of 100 nmol/kg/min for about one hour prior to and during circulation of the baboon's arterial blood past the prosthetic surface of the dialyzer (through the dialyzer capillaries). For comparative purposes, heparin was administered instead of PPACK in control studies. Heparin administration consisted of an initial bolus of 150 units (U) per kg of body weight followed by continuous infusion of 150 U/kg/hour for one hour prior to and during circulation of the baboon's arterial blood through the dialyzer. Inhibition of platelet deposition of the prosthetic (capillary) surface was determined by measuring the volume of saline held by the dialyzer before and after having arterial blood circulated through it.

As shown in FIG. 5, administration of PPACK inhibited dialyzer volume loss significantly better than heparin.

B. In another study with juvenile male baboons weighing between 9–13 kg, each animal received a chronic femoral "Scribner-type" arteriovenous silastic shunt. This permanent shunt system does not detectably activate platelets or coagulation. Harker et al., *J. Clin. Invest.*, 64:559–69 (1979); and Hanson et al., *Thromb. and Haem.*, 58(3):801–05 (1987). Hematocrits (33±1.6%) white blood cell counts (14±2×10³/μL) and fibrinogen concentrations (403±23 mg/dL) were all normal in the animals used. Animals with low hematocrits, elevated WBC, inadequate shunt blood flow or local inflammation were excluded from the study.

Each animal was studied four times. Two, two-hour exposures with PPACK were compared with two, two-hour exposures with heparin anticoagulation in the same animal. During each perfusion continuous blood flow from the shunts were measured by a Doppler ultrasonic flowmeter (L and M Electronics Model 1012, Daly City, Calif.). Blood flow rates range between 180 and 250 ml per minute.

Hollow fiber dialyzers (Travenol CF1211, Deerfield, Ill., USA) of the cuprophane hollow fiber type, were used. Each dialyzer was used twice on separate occasions, in the same animal, and with the same anticoagulant. Before each use and for overnight storage of the hemodialyzer, each dialyzer unit (cell) was primed with sterile normal saline solution. For reuse the dialyzers were stored a 4° C. overnight from about 12 to about 18 hours. During hemoperfusion the dialysate chamber was filled with sterile isotonic saline solution and the drainage ports were plugged. Medical grade silicone rubber tubing, 3.0 mm internal diameter (i.d.) (Dow-Corning Corporation, Midland, Mich.), and thin-walled Teflon tubing, 2 cm in length, were subsequently used to connect the dialyzers to the shunt.

Dialyzer fiber volume was determined before and after each use, as a measure of fiber thrombotic occlusion. Gotch et al., *Trans. of Amer. Soc. for Artificial Internal Organs*, 1969:87–96. Thus, prior to each use, the cell was filled with isotonic saline and all visible air was flushed from the fiber bundle. By attaching a manometer with a bulb to the arterial header and flushing with air for one minute at 45 torr, the water content of the cell was then recovered quantitatively from the venous header into a volumetric container. Two measurements were made at each time and averaged.

PPACK or standard heparin (from porcine intestinal mucosal, Invenex Laboratories, Chagrin Falls, Ohio) was infused into the arterial limb of the vascular shunt immediately proximal to the dialyzer. The heparin administration was given as an initial bolus of 100 U/kg, 5 min before introducing the dialyzer and subsequently by continuous infusion of 15 U/kg/hour for two hours using a Harvard microinfusion pump (Model 901, Harvard Apparatus Co. Inc.), PPACK was infused continuously at a rate of 100 nmol/kg per min for about 15 minutes, prior to and then during the 2 hours blood was circulated past the prosthetic surface of the dialyzer allowing for about fifteen minutes of preinfusion to achieve steady state levels.

In addition to measuring the loss of hollow fiber volume, the extent of platelet thrombus accumulation in the dialyzer fiber bundles was measured by scintillation camera (Picker Corp., Northford, Conn.) imaging of autologous $^{111}$In-labeled platelets remaining in the flushed dialyzer immediately after each use. Autologous baboon platelets were labeled with $^{111}$In-oxine (Amersham Corp., Arlington Heights, Ill.) and injected prior to insertion of the dialyzer. Kotze et al., *Thromb. and Haemstasis,* 53:404–07 (1985). Images of the "first use" dialyzers, giving counts per minute (cpm), were acquired immediately after the blood had been flushed from the system and after the determinations of fiber bundle volume had been complete. "Repeat-use" dialyzers were imaged prior to the second use to measure the residual $^{111}$In-platelet radioactivity. Total platelet deposition was then calculated by dividing the dialyzer cpm by the circulation blood cpm/ml, and multiplying this ratio by the number of platelets in 1 ml of blood.

Blood cell counts (platelets, white blood cells, and red blood cells) were performed on disodium EDTA anticoagulated whole blood using a J. T. Baker whole blood analyzer Model 810 (Allentown, Pa.). Hanson et al., *J. Clin. Invest.* 75:1591–99 (1985); and Hanson et al., *Arteriosclerosis,* 5:595–603 (1985). Standard template bleeding times, were performed on the shave volar surface of the forearm in a manner as described in Harker et al., *New. Eng. J. Med.,* 287:155–59 (1972) and Malpass et al., *Blood,* 57:736–40 (1981). Bleeding times were done in duplicate and averaged. Commercially available radioimmunometric assays were carried out to measure plasma levels of platelet factor 4 (PF4) (Abbott Laboratories, North Chicago, Ill.), β-thromboglobulin (βTG) (Amersham Corporation, Arlington Heights, Ill.), fibrinopeptide A (FPA) (MICRO USA Inc., New York, N.Y.) and activated complement C3 antigen (C3a) (Amersham Corp.). Blood samples for these plasma assays were collected, processed and determined as described in the procedures of Example 1 and in Malpass et al., ibid. and Hanson et al., *Arteriosclerosis,* 5:595–603 (1985). Activated thromboplastin times (APTT) were performed using a standard method (Activated PTT reagent, Ortho Diagnostics, Raritan, N.J.). A fibrometer (Fibrosystem, Division of Becton and Dickinson and Co., Cockeysville, Mass.) was used for endpoint clot detection as described in Biggs, R., Human Blood Coagulation, Haemostasis and Thrombosis, Oxford, Blackwell Scientific, pages 657–750 (1976). Fibrinogen was determined by a total clottable protein method described by Jacobsson K., *Scand. J. Clin. Lab. Invest.,* 7(Suppl. 14):9–54 (1955).

The plasma activity levels of heparin and PPACK were determined on blood samples collected in 3.8% sodium citrate and ACD respectively. Samples were centrifuged (2000×g, for 5 min) immediately after collection and the recovered plasma was frozen until assay. Heparin and PPACK activity levels were determined after 30 and 60 minutes of continuous infusion. In some studies PPACK levels were determined at three sites: (i) systemic (ii) immediately proximal to the dialyzer but distal to the site of the PPACK infusion, and (iii) immediately distal to the dialyzer. Levels of heparin activity were determined by measuring the potentiating effect of heparin of plasma anti-Xa activity using a synthetic chromogenic substrate (Stachrom Heparin, Stago, France). Teien et al., *Thrombo Research,* 10:399–410 (1977). PPACK levels were determined by measuring antithrombin activities using a standard thrombin reagent (Bovine Thrombin, Parke-Davis, Morris Plains, N.J.). The results were expressed as µg/ml from a PPACK calibration curve obtained in autologous baboon ACD plasma.

Platelet aggregation was carried out in citrated platelet-rich plasma (PRP) using a Chronolog platelet aggreometer (Havertown, Pa.) by recording the increase in light transmission through a stirred suspension of PRP at 37° C. Citrate concentration was held constant at 0.12M and the platelet count of PRP was adjusted to 250,000 plat/µl. The results were expressed as $EC_{50}$ (that concentration of agonist producing 50% of the maximal aggregation response) induced by collagen (Hormon-Chemie, Munchen) and ADP (Sigma Chemical Co., St. Louis, Mo.) as reported in Malpass et al., *Blood,* 57:736–40 (1981).

In comparing the effects of heparin and PPACK on coagulation, doses were selected that produced similar prolongations of the APTT (Table 5). For heparin the APTT was systemic blood was prolonged to 199±18 seconds throughout the period of blood exposure to the hemodialyzer at a rate of 100 U/kg initial bolus and 15 U/kg per hour by a continuous infusion thereafter which corresponded to a plasma level of 1.06±0.08 U/ml. For PPACK the APTT with venous blood was prolonged to 139±23 seconds at a rate of 100 nmol/kg per min infused proximal to the dialyzer, corresponding to a systemic plasma level of 1.52±0.06 µg/ml. PPACK, but not heparin, prevented the increase in plasma levels of FPA, the thrombin cleavage product of fibrinogen (Table 5).

TABLE 5

| Comparison of the Anticoagulating Effects of Heparin and PPACK | | | |
|---|---|---|---|
| Plasma Determinations | Control | Heparin | PPACK |
| APTT (sec) | 34 ± 1 | 199 ± 18 | 139 ± 23 |
| Heparin (units/ml) | — | 1.1 ± 0.08 | — |
| PPACK (µg/ml) | — | — | 1.5 ± 0.06 |
| FPA (pmol/l) | 6.2 ± 0.68 | 9.2 ± 3.1 | 1.8 ± 0.20 |
| Fibrinogen (mg/dL) | 403 ± 24 | 387 ± 32 | 344 ± 14.0 |

Since PPACK was infused directly into the dialyzer and removal from the circulation was rapid, the intradevice levels of this reagent were substantially greater than the systemic concentrations (Table 6).

TABLE 6

| PPACK Concentrations in Plasma Entering, and Exiting Hollow-fiber Dialyzer Compared with Systemic Levels | | |
|---|---|---|
| | Plasma PPACK (µg/ml) Time Period (min) | |
| Sample Site | 30 | 60 |
| Systemic | 1.4 ± 0.40 | 1.6 ± 0.50 |
| Predialyzer | 3.05 ± 0.55 | 3.65 ± 0.65 |

TABLE 6-continued

PPACK Concentrations in Plasma Entering, and
Exiting Hollow-fiber Dialyzer Compared with Systemic Levels

| Sample Site | Plasma PPACK (μg/ml) Time Period (min) | |
|---|---|---|
| | 30 | 60 |
| Postdialyzer | 3.9 ± 0.50 | 4.1 ± 1.20 |

The platelet reactivity was evaluated by comparing whole blood platelet count, bleeding time, platelet aggregation, and plasma levels of the platelet-specific α granule proteins βTG and PF4 (Table 7). whereas the platelet counts were not significantly changed during exposure to the dialyzer during administration of either heparin or PPACK, significant differences were apparent with respect to platelet hemostatic function. PPACK markedly prolonged bleeding times and decreased the release from platelets into plasma of PF4 and βTG; heparin failed to affect any of these determinations (Table 7). Platelet aggregations, performed in 5 other animals receiving 100 nmol/kg per min PPACK, included by either ADP or collagen was essentially normal (Table 7).

TABLE 7

Effects of Heparin and PPACK on Platelets

| Determination | Control | Heparin | PPACK | Differences (Heparin v. PPACK) |
|---|---|---|---|---|
| Platelet Count (× $10^3$/μL) | 449 ± 90 | 420 ± 28 | 401 ± 17 | >0.5 |
| Bleeding Time (min) | 4.5 ± 0.4 | 6.7 ± 1.2 | 24.8 ± 1.9 | >0.001 |
| Plasma | | | | |
| PF4 (ng/ml) | 8.2 ± 1.0 | 20.7 ± 6.8 | 4.5 ± 0.7 | <0.01 |
| βTG (ng/ml) | 13.5 ± 2.4 | 23.7 ± 6.6 | 11.5 ± 5.7 | <0.01 |
| Platelet Aggregation ($EC_{50}$) | | | | |
| ADP (μmol/L) | 2.35 | — | 2.8 | |
| Collagen (μg/ml) | 1.9 | — | 3.15 | |

Dialyzer fiber bundle volume (DFV) and $^{111}$In-platelet deposition within the fiber bundle were used as independent measures of thrombus formation in the dialyzers after each use (FIG. 8). Heparin-treated animals had significant and progressive losses of DFV and reciprocal increases in platelet accumulation within the fiber bundle at all times tested. By contrast, the PPACK treatment preserved DFV with a marked reduction of platelet accumulation in the dialyzers.

No apparent difference was found between heparin and PPACK therapy with respect to complement activation (C3a) or decrease in white blood cells counts during dialyzer use. C3a levels increased from a control level of 769±202 ng/ml to a peak level of 2005±728 ng/ml and 1989±360 ng/ml for heparin and PPACK respectively. Conversely, an early fall in white blood cell count from control was observed (14,100±1,000 cells/ul to 6,200±860 cells/uLfor heparin and to 5,900±810 cells/ul for PPACK.

The results of the this study and that of Part A demonstrate that infusion of the synthetic antithrombin PPACK during hemodialysis markedly reduces platelet-dependent thrombus formation and consequent hollow fiber bundle volume loss in the hemodialyzer devices in contrast to the findings in heparin anticoagulated control experiments. Moreover, other indirect blood markers of thrombus formation in vivo, i.e., plasma PF4, βTG and FPA remained at basal levels after PPACK infusion, in contrast with the elevated levels observed during heparin therapy. PPACK, but not heparin, also inhibited platelet hemostatic plug formation as shown by the prolonged bleeding times, without altering measurements of platelet aggregation induced by either collagen of ADP ex vivo. These results provide evidence that the progressive loss of dialyzer hollow fibers is a platelet-dependent, thrombin-mediated, occlusive thrombotic process.

Hemodialysis with hollow fiber dialyzers is used in uremic patients undergoing chronic maintenance dialysis in the United States. Preservation of the function for dialyzer reuse has become an important consideration not only for economic reasons, but also in view of recent epidemiologic studies which have shown that mortality and morbidity decrease with device reuse. Bok et al., Proc. Council Dial. Transplant, 10:92–9 (1980). However, despite heparinization, blood contact with the artificial surface of the dialyzer activates complement, platelets and coagulation resulting in transient neutropenia, thrombus formation and progressive loss in DFV and eventually dialyzer transport function. Chenowith, et al., Artificial Orgn., 11:155–62 (1987); Salzman, E., Fed. Proc., 30:1503–09 (1971); and Vroman et al., Fed. Proc., 30:1494–502 (1971). Additionally, activation and/or cleavage products resulting from the blood-surface interaction may produce untoward systemic effects such a hypotension and respiratory distress. Henderson et al., Blood Purif., 1:3–8 (1985); and Dangiradas, et al., Kidney In., 1:190–96 (1972). Other adverse reactions associated with heparin use include abnormal bleeding (especially gastro-intestinal and intracranial) [Lindsay et al., Lancet, 2:1287–90 (1972); Dangiradas et al., Kidney Int., 1:190–96 (1972)], heparin-induced thrombocytopenia [Cines et al., New Eng. J. Med.. 303:788–95 (1980)], with bone repair and possibly severe decalcifying bone disease. Squires et al., JAMA, 241:2417–18 (1979); and Glowacki, J., Life Sci., 33:1019–24 (1983). Moreover, protamine, which is given to reverse heparin anticoagulation at the end of dialysis, may also cause problems such as hypotension and complement release. Anderson et al., Surgery, 46:1050 (1959) and Loubser, P. G., Texas Heart J., 14:369–73 (!987). Occasionally commercial heparin has been associated with arterial thrombosis, presumably due to the effect of some contaminating platelet-activating fraction(s). Salzman et al., J. Clin. Invest., 65:64–73 (1980).

PPACK is removed rapidly both from the circulation ($T_{50}$ removal rate of less than 3 min) Collen et al., J. Lab. and Clin. Med., 99:76–83 (1982) and likely through the dialyzing membrane because of its small molecular size, it is feasible to maintain antithrombotic levels locally in the dialyzer with little or no systemic antihemostatic effects. For example, in the present study the measured plasma anticoagulant activity within the dialyzer was markedly elevated compared with the systemic level when 100 nmol/kg per min was administered (Table 7). Under actual dialyzing conditions, the difference would be even more striking because PPACK would also be cleared into the dialysate. Thus, the resultant hemostatic burden is minimal as compared to heparin. Although heparin is not entirely safe or effective, it continues to be used in dialysis patients because no suitable alternative has been available. The present invention thus provides an improved method of performing hemodialysis.

The foregoing is intended as illustrative of the present invention but not limiting. Numerous variations and modifications may be effected without departing from the true spirit and scope of the invention.

What is claimed is:

1. A method of inhibiting platelet dependent arterial thrombosis in a patient which method comprises administering to said patient a therapeutically effective amount of peptide represented by Formula 1

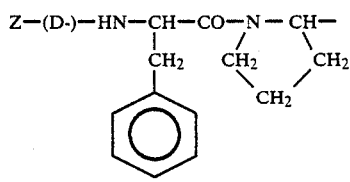
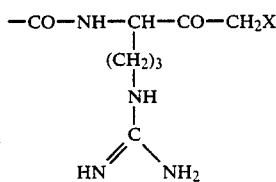

wherein Z is hydrogen or a $C_1$-$C_6$ acyl; X is a halogen atom; and the hydrohalic acid addition products thereof.

2. The method of claim 1 wherein X is chlorine and Z is hydrogen.

3. A method of inhibiting arterial restenosis in a patient, which method comprises:
   (a) administering to said patient a therapeutically effective amount of a peptide represented by Formula 1

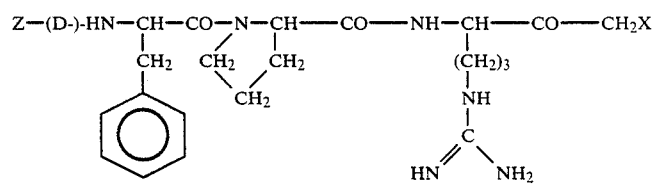

wherein Z is hydorgen or a $C_1$-$C_6$ acyl group; X is a halogen atom; and the hydrohalic acid addition products thereof,
   (b) subjecting said patient to endarterectomy, angioplasty or treatment with a therapeutically effective amount of a thrombolytic agent to increase the blood flow channel diameter in a stenosed artery to produce a treated artery, and
   (c) circulating arterial blood of said patient through said treated artery.

4. The method of claim 3 wherein the amount of said peptide is sufficient to achieve a peptide concentration in the blood of at least 0.2 ug/ml.

5. The method of claim 3 wherein the amount of said peptide is sufficient to achieve a peptide concentration in the blood of at least 1 ug/ml.

6. The method of claim 5 wherein the amount of said peptide is sufficient to maintain said peptide concentration for a time period of at least 5 minutes.

7. The method of claim 5 wherein the amount of said peptide is sufficient to maintain said concentration of the blood for a time period of at least 5 minutes but no more than 90 minutes.

8. The method of claim 3 wherein X is chlorine and Z is hydrogen.

9. The method of claim 3 wherein said thrombolytic agent is streptokinase, urokinase or tissue plasminogen activator.

10. The method of claim 3 wherein (a) is performed prior to (c).

11. The method of claim 10 wherein (c) is performed while said peptide concentration in the blood is at least 1 ug/ml.

12. The method of claim 10 wherein (c) is performed within 5 minutes of performing (a).

13. A method of inhibiting platelet deposition on an arterial prosthetic surface in a patient, which method comprises:
   (a) administering to said patient a therapeutically effective amount of a peptide represented by Formula 1

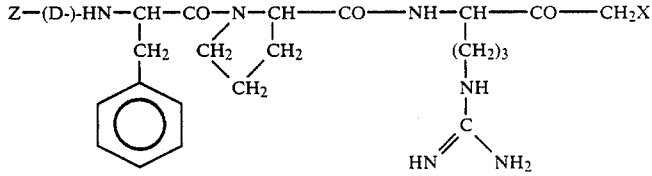

wherein Z is hydrogen or $C_1$-$C_6$ acyl group; X is a halogen atom; and the hydrohalic acid addition products thereof,
   (b) contacting circulating arterial blood of said patient with a prosthetic surface.

14. The method of claim 13 wherein the amount of said peptide is sufficient to achieve a peptide concentration in the blood of at least 0.2 ug/ml.

15. The method of claim 13 wherein the amount of said peptide is sufficient to achieve a peptide concentration in the blood of at least 1 ug/ml.

16. The method of claim 15 wherein the amount of said peptide is sufficient to maintain said peptide concentration for a time period of at least 5 minutes.

17. The method of claim 15 wherein the amount of said peptide is sufficient to maintain said concentration in the blood for a time period of at least 5 minutes but no more than 90 minutes.

18. The method of claim 16 wherein X is chlorine and Z is hydrogen.

19. The method of claim 13 wherein said thrombogenic surface is an arterial prosthesis or an arteriovenous shunt.

20. The method of claim 13 wherein (a) is performed prior to (b).

21. The method of claim 20 wherein (b) is performed while said peptide concentration in the blood is at least 0.2 ug/ml.

* * * * *

UNITED STATES PATENT AND TRADEMARK OFFICE
CERTIFICATE OF CORRECTION

PATENT NO. : 4,929,602  
DATED : May 29, 1990  
INVENTOR(S) : Laurence A. Harker and Stephen R. Hanson Page 1 of 1

It is certified that error appears in the above-identified patent and that said Letters Patent is hereby corrected as shown below:

Column 1,
Line 5, insert:

-- This invention was made with government support under Grant Nos. HL 31950 and HL 31469 from the National Institutes of Health. The U.S. government may have certain rights in the invention. --

Signed and Sealed this

Seventh Day of May, 2002

*Attest:*

JAMES E. ROGAN
*Director of the United States Patent and Trademark Office*

*Attesting Officer*